(12) United States Patent
Fei et al.

(10) Patent No.: US 10,076,476 B2
(45) Date of Patent: Sep. 18, 2018

(54) ORAL CARE COMPOSITIONS COMPRISING A PEROXIDE SOURCE, A POLYHYDRIC ALCOHOL, AND A SURFACTANT

(71) Applicant: Colgate-Palmolive Company, New York, NY (US)

(72) Inventors: Lin Fei, Kendall Park, NJ (US); Suman Chopra, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/528,926

(22) PCT Filed: Dec. 9, 2015

(86) PCT No.: PCT/US2015/064725
§ 371 (c)(1),
(2) Date: May 23, 2017

(87) PCT Pub. No.: WO2016/094523
PCT Pub. Date: Jun. 16, 2016

(65) Prior Publication Data
US 2017/0312195 A1 Nov. 2, 2017

Related U.S. Application Data

(60) Provisional application No. 62/090,182, filed on Dec. 10, 2014.

(51) Int. Cl.
```
A61K 8/22    (2006.01)
A61K 8/49    (2006.01)
A61K 8/34    (2006.01)
A61K 8/27    (2006.01)
A61K 8/81    (2006.01)
A61Q 11/00   (2006.01)
A61K 8/37    (2006.01)
```
(52) U.S. Cl.
CPC ............... *A61K 8/22* (2013.01); *A61K 8/345* (2013.01); *A61K 8/375* (2013.01); *A61K 8/4973* (2013.01); *A61K 8/8176* (2013.01); *A61Q 11/00* (2013.01)

(58) Field of Classification Search
CPC ... A61K 8/38; A61K 8/30; A61K 8/34; A61K 8/37; A61K 8/22
USPC .......................................................... 424/53
See application file for complete search history.

(56) References Cited

U.S. PATENT DOCUMENTS

| | | | |
|---|---|---|---|
| 3,657,413 A | 4/1972 | Rosenthal | |
| 4,431,631 A * | 2/1984 | Clipper | A61K 8/22 424/53 |
| 4,837,008 A | 6/1989 | Rudy et al. | |
| 4,839,157 A | 6/1989 | Mei-King Ng et al. | |
| 6,555,512 B1 | 4/2003 | Coggeshall et al. | |
| 6,746,679 B2 * | 6/2004 | Nathoo | A61K 8/042 424/401 |
| 9,370,472 B2 | 6/2016 | Fei et al. | |
| 2003/0133884 A1 | 7/2003 | Chang et al. | |
| 2007/0280894 A1 * | 12/2007 | Romano | A61K 8/22 424/53 |
| 2008/0193392 A1 | 8/2008 | Kwak et al. | |

FOREIGN PATENT DOCUMENTS

| | | |
|---|---|---|
| EP | 2349189 | 8/2015 |
| JP | 2011-225671 | 11/2011 |
| WO | WO 1988/006879 | 9/1988 |
| WO | WO 2011/087786 | 7/2011 |
| WO | WO 2012/145611 | 10/2012 |
| WO | WO 2014/134502 | 5/2014 |
| WO | WO 2014/092733 | 6/2014 |

OTHER PUBLICATIONS

International Search Report and Written Opinion in International Application No. PCT/US2015/064725, dated Mar. 16, 2016.

* cited by examiner

*Primary Examiner* — Walter E Webb

(57) ABSTRACT

Provided is an oral care composition comprising a peroxide source, a polyhydric alcohol and a surfactant system having an HLB value of from 4 to 13, wherein the combined amount of the polyhydric alcohol and the surfactant system is from 60 weight % to 95 weight % by total weight of the composition, and wherein the weight ratio of the polyhydric alcohol to the surfactant system is from 9:1 to 1:4. The composition is resistant to peroxide decomposition.

22 Claims, No Drawings

ORAL CARE COMPOSITIONS COMPRISING A PEROXIDE SOURCE, A POLYHYDRIC ALCOHOL, AND A SURFACTANT

CROSS-REFERENCE TO RELATED PATENT APPLICATIONS

This application claims the benefit of priority to U.S. Provisional Patent Application Ser. No. 62/090,182 filed Dec. 10, 2014, the entirety of which is incorporated herein by reference.

BACKGROUND

Oral care compositions comprising peroxide sources are useful for cleaning and whitening teeth. The peroxide may be present as hydrogen peroxide, or as a source of bound hydrogen peroxide. Sources of bound hydrogen peroxide include polyvinylpyrrolidone (PVP)-$H_2O_2$ complexes, urea peroxide, calcium peroxide and sodium percarbonate. The peroxide can bleach teeth, remove stains, and kill cariogenic bacteria. However, peroxide compounds are highly reactive with common ingredients found in oral care formulations. Moreover, hydrogen peroxide can spontaneously decompose to form oxygen gas and water, so that on storage, the composition containers may bloat, burst or leak. Consequently, the remaining formulation will have a reduced whitening and cleaning efficacy. Some formulations initially comprise very high levels of peroxide, which decomposes over time, so that the exact amount of peroxide delivered on application is variable and largely dependent on how long and under what conditions the formulation has been stored.

There is therefore a need for improved peroxide-containing oral care compositions which exhibit improved stability of the peroxide, and which are therefore suitable for long-term storage without a significant loss of whitening and cleaning efficacy.

BRIEF SUMMARY

The present inventors have unexpectedly found that in an oral care composition comprising a peroxide source and a carrier comprising a polyhydric alcohol, the stability of the peroxide may be increased by increasing the hydrophobicity of the composition. Specifically, oral care compositions with liquid carriers typically have an HLB value of at least 16. However, the inventors of the present application have discovered that when the HLB value is lowered below 14, stability of the peroxide source is increased.

Accordingly, in a first aspect there is provided an oral care composition comprising a peroxide source, a polyhydric alcohol and a surfactant system having an HLB value of from 4 to 13, wherein the combined amount of the polyhydric alcohol and the surfactant system is from 60 weight % to 95 weight % by total weight of the composition, and wherein the weight ratio of the polyhydric alcohol to the surfactant system is from 9:1 to 1:4.

Preferably, the polyhydric alcohol is selected from propylene glycol, polyethylene glycol, glycerin, and mixtures thereof. Most preferably, the polyhydric alcohol is propylene glycol.

Optionally, the surfactant system has an HLB value of from 4 to 13. Preferably, the surfactant system has an HLB value of from 4 to 9. Preferably, the surfactant system has an HLB value of from 5 to 8. Most preferably, the surfactant system has an HLB value of 5, 6, 7 or 8.

Optionally, the weight ratio of the polyhydric alcohol to the surfactant system is from 9:1 to 1:2 or from 9:1 to 1:1. Preferably, the weight ratio of the polyhydric alcohol to the surfactant system is from 7:3 to 1:1. More preferably, the weight ratio of the polyhydric alcohol to the surfactant system is from 3:2 to 1:1.

Optionally, the combined amount of the polyhydric alcohol and the surfactant system is from 70 weight % to 95 weight % or from 80 weight % to 90 weight %, by total weight of the composition. Preferably, the combined amount of the polyhydric alcohol and the surfactant system is from 85 weight % to 90 weight % by total weight of the composition.

Optionally, the surfactant system having an HLB value from 4 to 13 comprises a non-ionic surfactant, an amphoteric surfactant, or combinations thereof. Optionally, the surfactant system having an HLB value from 4 to 13 comprises propylene glycol monocaprylate. Further optionally, the surfactant system having an HLB value from 4 to 13 comprises sorbitan laurate. Still further optionally, the surfactant system having an HLB value from 4 to 13 comprises polyethylene glycol caprylate/caprate glyceride.

Optionally, the peroxide source is selected from: hydrogen peroxide, urea peroxide, sodium percarbonate, sodium perborate, polyvinylpyrrolidone-hydrogen peroxide complex, and mixtures thereof. Preferably, the peroxide source is polyvinylpyrrolidone-hydrogen peroxide complex.

Optionally, the peroxide source is present in the composition to deliver hydrogen peroxide in an amount of 0.1 weight % to 5 weight % by total weight of the composition. Preferably, the peroxide source is present in the composition to deliver hydrogen peroxide in an amount of 1 weight % to 3 weight % by total weight of the composition.

Optionally, the composition further comprises an agent selected from: surfactants, desensitizing agents, tartar control agents, binders, thickening agents, detergents, adhesion agents, foam modulators, pH modifying agents, mouth feel agents, sweeteners, flavorants, colorants, humectants, fluoride sources and combinations thereof. Further optionally, the composition is selected from whitening gels, mouthwashes, sprays, dentifrices, oral strips, chewing gums and lozenges.

In a second aspect, there is provided a use of a surfactant system having an HLB value of from 4 to 13 to stabilize a peroxide source in an oral care composition, wherein the composition comprises, in addition to the peroxide source and the surfactant system having an HLB value of from 4 to 13, a polyhydric alcohol, wherein the combined amount of the polyhydric alcohol and the surfactant system is from 60 weight % to 95 weight % by total weight of the composition, and wherein the weight ratio of the polyhydric alcohol to the surfactant is from 9:1 to 1:4.

Preferably, the composition is as defined herein.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

In one arrangement, there is provided an oral care composition comprising a peroxide source, a polyhydric alcohol and a surfactant system having an HLB value of from 4 to 13.

In a preferred aspect, the combined amount of the polyhydric alcohol and the surfactant system is from 60 weight % to 95 weight % by total weight of the composition, and the weight ratio of the polyhydric alcohol to the surfactant system is from 9:1 to 1:4.

Polyhydric Alcohol

The term "polyhydric alcohol" refers to an organic compound comprising two or more hydroxyl groups. Preferably, the polyhydric alcohol is selected from propylene glycol, polyethylene glycol (preferably with a molecular weight of from 400 to 800, or 400 to 600), glycerin, and mixtures thereof. Most preferably, the polyhydric alcohol is propylene glycol. Other suitable polyhydric alcohols include sorbitol, xylitol, PEG 400 and PEG 600.

In one arrangement, the composition comprises at least one polyhydric alcohol in an amount of from 12 weight % to 85 weight % by total weight of the composition, or from 20 weight % to 60 weight % by total weight of the composition or from 20 weight % to 40 weight % by total weight of the composition. In some embodiments, the composition comprises at least one polyhydric alcohol in an amount of from 30 weight % to 80 weight %, from 30 weight % to 70 weight %, from 30 weight % to 60 weight %, from 30 weight % to 50 weight %, or from 30 weight % to 40 weight %, by total weight of the composition. In other embodiments, the composition comprises at least one polyhydric alcohol in an amount of from 40 weight % to 80 weight %, from 40 weight % to 70 weight %, from 40 weight % to 60 weight %, or from 40 weight % to 50 weight %, or from 40 weight % to 45 weight %, by total weight of the composition. In further embodiments, the composition comprises at least one polyhydric alcohol in an amount of from 50 weight % to 80 weight %, from 50 weight % to 70 weight %, from 50 weight % to 60 weight %, or from 50 weight % to 55 weight %, by total weight of the composition.

Surfactant System

The surfactant system may comprise or consist of one or more surfactants. In one embodiment, the surfactant system comprises a non-ionic surfactant. In some embodiments, the non-ionic surfactant is selected from: sorbitan esters and ethoxylated sorbitan esters (for example PEG-20 sorbitan isostearate, sorbitan monolaurate, polysorbate-20, polysorbate-40, polysorbate-60, polysorbate-80); ethoxylates (for example, Ceteth-20, PEG-30 castor oil, PEG-40 hydrogenated castor oil, PEG-60 hydrogenated castor oil, Laureth-7, Isolaureth-6, Steareth-10, Steareth-20, Steareth-21, Steareth-100, Ceteareth-12, Oleth-5, Oleth-10, and Oleath-20); ethoxylated adducts (for example, PEG-25 stearate, glyceryl stearate and PEG-100 stearate); PEG esters (for example, PEG-8 oleate, PEG-8 laurate, PEG-8 dilaurate, PEG-12 dilaurate, PEG-80 diisostearate, PEG-40 stearate); propoxylates (for example, PPG-10 butanediol, PPG-50 oleyl ether, PPG-2-ceteareth-9, PPG-3-deceth-3, PPG-5-ceteth-20); ethoxylated modified triglycerides (for example, PEG-20 corn glycerides, PEG-12 palm kernel glycerides); alkylphenol aromatic ethoxylates (for example, dinonylphenol ethoxylate with 9 moles of EO, octylphenol ethoxylate with 20 moles of EO, octylphenol ethoxylate with 40 moles of EO); and block copolymers which are alkoxylated glycols having ethoxylated and propoxylated segments (for example, Poloxamers 182 and 234, and Meroxapol 174).

In other embodiments, the surfactant system comprises a surfactant selected from: ethoxylated alcohols such as steareth-2, Oleth-3, nonoxynol-2, PPG-4-Ceteth-1; ethoxylated carboxylic acids such as PEG-4 dilaurate, PEG-2 oleate; glyceryl esters such as PEG-2 castor oil, PEG-7 hydrogenated castor oil, glyceryl monooleate, glyceryl monostearate, triglycerol monooleate, decaglyceryl tetraoleate, and polyglyceryl-3 oleate, glyceryl stearate; sorbitan derivatives such as sorbitan oleate, sorbitan monostearate, sorbitan tristearate, sorbitan monooleate, sorbitol trioleate, sorbitan monotallate, sorbitan isostearate; sugar esters such as sucrose distearate; and lanolin alcohol.

In a preferred arrangement, the surfactant system comprises one or more of propylene glycerol monocaprylate (for example, Capryol 90® from Gattefosse), sorbitan laurate (Span 20® from Croda) and polyethylene glycol caprylate/caprate glyceride. In another arrangement, the surfactant system consists of: propylene glycerol monocaprylate (for example, Capryol 90® from Gattefosse), sorbitan laurate (Span 20® from Croda) or polyethylene glycol caprylate/caprate glyceride Other particularly preferred surfactants that may be incorporated in the surfactant system include sorbitan monooleate (Span 80®), polysorbate, alcohol ethoxylate (Neodol 45-7®), Steareth-2 and propylene oxide/polyethylene oxide copolymer (Pluronic P-123®).

The HLB value defines the hydrophilic to lipophilic balance of the surfactant system. The HLB parameter is a well-known parameter, the calculation of which is disclosed and explained in numerous references. For nonionic surfactants, data obtained by actual analysis is usually a more accurate measure of HLB values than theoretical determinations. For purposes of this invention it is intended that either the actual or theoretical HLB value may be used as the basis for selection.

HLB values of surfactants may be calculated by experimental and theoretical methods that are known to the person skilled in the art of physical chemistry.

An exemplary and commonly used experimental method for determining the HLB value of an unknown surfactant involves blending the unknown surfactant in varying ratios with an emulsifier of known HLB, and using the blend to emulsify an oil of known "required HLB" (the "required HLB" of an oil refers to the HLB of an emulsifier that would optimally stabilize an emulsion comprising the oil). The blend which performs best is assumed to have an HLB that is approximately equal to the "required HLB" of the oil such that the HLB value of the unknown surfactant can be calculated. (Experimental protocols for determining HLB values are further described in "The HLB system—a time-saving guide to emulsifier selection; ICI Americas Inc, Wilmington, Del. 19897).

An exemplary and commonly used theoretical method for calculating HLB for nonionic products is the Griffin formula: $HLB = 20 \times MW_H/(MW_H + MW_L) =$ wt % hydrophile/5, wherein $MW_H$=mol. wt of hydrophile and $MW_L$=mol. wt. of hydrophobe. (Griffin, William C. (1954), "Calculation of HLB Values of Non-Ionic Surfactants," *Journal of the Society of Cosmetic Chemists* 5 (4): 249-56).

Another exemplary and commonly used theoretical method is Davies' group contribution method (Davies J T: "A quantitative kinetic theory of emulsion type, I. Physical chemistry of the emulsifying agent," Gas/Liquid and Liquid/Liquid Interface. Proceedings of the International Congress of Surface Activity (1957): 426-438). According to this method of calculation, negative values are assigned to the lipophilic groups in a surfactant molecule and positive values are assigned to the hydrophilic groups in a surfactant molecule. The HLB of a given surfactant is essentially calculated by adding to the number 7 the sum of the positive values representing the hydrophilic groups and by subtracting the negative values representing the hydrophobic groups. The HLB scale ranges from 1 to 20. The lower the HLB value, the more lipophilic or oil-soluble the surfactant is. The higher the HLB value, the more water-soluble or hydrophilic the surfactant is. Depending on the formula chosen for HLB calculation, the HLB value will be slightly different. HLB can also be obtained through experiment, and value will also be slightly different from the calculation. Value with +/−0.5 in difference is normal.

HLB values are additive. Thus, if the surfactant system comprises more than one surfactant, the HLB of the system is calculated by determining the weighted HLB of all the surfactants, based on the concentration of each surfactant. (For example, a blend comprising 70% Tween 80 having an HLB value of 15 and 30% SPAN 80 having an HLB value of 4.3 would have an overall HLB of (0.7×15)+(0.3×4.3)= 11.8).

In some embodiments, the surfactant system has an HLB value of from 4 to 13, from 4 to 10, from 4 to 9, from 4 to 8, from 4 to 7, or from 4 to 6. In other embodiments, the surfactant system has an HLB value of from 5 to 13, from 5 to 10, from 5 to 9, from 5 to 8, from 5 to 7, or from 5 to 6. In further embodiments, the surfactant system has an HLB value of from 6 to 13, from 6 to 10, from 6 to 9, or from 6 to 8. In still further embodiments, the surfactant system has an HLB value of from 7 to 13, from 7 to 10, or from 7 to 9. Preferably, the surfactant system has an HLB value of from 5 to 9 or from 5 to 8.

The present inventors have found that when the HLB value is 14 or above, the surfactant system no longer has any stabilizing effect on the peroxide. When the HLB value is below 4, the surfactant system is not soluble in the polyhydric alcohol carrier. Without wishing to be bound by theory, it is believed that by increasing the hydrophobicity of the environment of the polyhydric alcohol carrier, electron transfer between molecules that occurs in the redox reaction leading to peroxide degradation, is diminished or retarded.

In one arrangement, the composition comprises a surfactant system as defined herein in an amount of from 5 weight % to 80 weight %, 5 weight % to 70 weight %, 5 weight % to 60 weight %, or from 5 weight % to 50 weight %, 5 weight % to 40 weight %, or from 5 weight % to 30 weight %, by total weight of the composition. In some embodiments, the composition comprises a surfactant system as defined herein in an amount of from 10 weight % to 60 weight %, from 10 weight % to 50 weight %, from 10 weight % to 40 weight %, from 10 weight % to 30 weight %, or from 10 weight % to 20 weight %, by total weight of the composition. In other embodiments, the composition comprises a surfactant system as defined herein in an amount of from 20 weight % to 60 weight %, from 20 weight % to 50 weight %, from 20 weight % to 40 weight %, from 20 weight % to 30 weight %, or from 20 weight % to 25 weight %, by total weight of the composition. In further embodiments, the composition comprises a surfactant system as defined herein in an amount of from 30 weight % to 60 weight %, from 30 weight % to 50 weight %, or from 30 weight % to 40 weight %, by total weight of the composition. In still further embodiments, the composition comprises a surfactant system as defined herein in an amount of from 40 weight % to 60 weight %, or from 40 weight % to 50 weight %, by total weight of the composition.

In one arrangement, the combined amount of the polyhydric alcohol and the surfactant system is from 60 weight % to 95 weight %, from 70 weight % to 95 weight %, from 75 weight % to 95 weight %, from 80 weight % to 95 weight %, from 85 weight % to 95 weight %, or from 90 weight % to 95 weight %, by total weight of the composition. In another arrangement, the combined amount of the polyhydric alcohol and the surfactant system is from 60 weight % to 90 weight %, from 60 weight % to 80 weight % or from 60 weight % to 70 weight % by total weight of the composition. In a further arrangement, the combined amount of the polyhydric alcohol and the surfactant system is from 70 weight % to 90 weight %, or from 80 weight % to 90 weight % or from 70 weight % to 95 weight %, or from 80 weight % to 95 weight % by total weight of the composition. In a still further arrangement, the combined amount of the polyhydric alcohol and the surfactant system is from 82 weight % to 90 weight %, from 87 weight % to 90 weight %, from 82 weight % to 88 weight %, or from 85 weight % to 88 weight %, by total weight of the composition.

Whilst any of the amounts of polyhydric alcohol provided above may be used in combination with any of the amounts of the surfactant system provided above, preferred embodiments are described below: In one embodiment, the amount of polyhydric alcohol is from 20 weight % to 80 weight %, and the amount of the surfactant system is from 8 weight % to 70 weight %, respectively, by total weight of the composition. In another embodiment, the amount of polyhydric alcohol is from 40 weight % to 80 weight %, and the amount of the surfactant system is from 8 weight % to 50 weight %, respectively, by total weight of the composition. In another embodiment, the amount of polyhydric alcohol is from 40 weight % to 60 weight %, and the amount of the surfactant system is from 25 weight % to 45 weight %, respectively, by total weight of the composition. In yet a further embodiment, the amount of polyhydric alcohol is from 50 weight % to 80 weight %, and the amount of the surfactant system is from 8 weight % to 30 weight %, respectively, by total weight of the composition. In these embodiments, the combined amount of the polyhydric alcohol and the surfactant system may be as defined above.

Weight Ratio of the Polyhydric Alcohol to the Surfactant System

In one arrangement, the weight ratio of the polyhydric alcohol to the surfactant system is from 9:1 to 1:4. Optionally, the weight ratio of the polyhydric alcohol to the surfactant system is from 9:1 to 1:3, from 9:1 to 1:2, from 9:1 to 1:1, from 9:1 to 3:2, from 9:1 to 7:3, or from 9:1 to 4:1. In some embodiments, the weight ratio of the polyhydric alcohol to the surfactant system is from 4:1 to 1:4, from 4:1 to 1:3, from 4:1 to 1:2, from 4:1 to 1:1, from 4:1 to 3:2, or from 4:1 to 7:3. In further embodiments, the weight ratio of the polyhydric alcohol to the surfactant system is from 7:3 to 1:4, from 7:3 to 1:3, from 7:3 to 1:2, from 7:3 to 1:1, or from 7:3 to 3:2. Preferably, the weight ratio of the polyhydric alcohol to the surfactant system is from 7:3 to 1:1 or from 3:2 to 1:1.

The present inventors have found that when a surfactant system having the HLB values defined above is used in combination with a polyhydric alcohol carrier in the amounts and/or ratios defined above, there is improved peroxide stability (i.e. less decomposition to oxygen and water), as compared to using the polyhydric alcohol carrier alone.

Peroxide Source

The compositions provided herein comprise a peroxide source. Suitable peroxide sources include hydrogen peroxide, peroxides of alkali and alkaline earth metals, organic peroxide compounds and peroxy acids and salts thereof. The term "peroxide source" includes any orally acceptable compound that delivers a perhydroxyl ion (OOH$^-$). A peroxide source can optionally be present in a form of a polymer-peroxide complex, for example a polyvinylpyrrolidone-hydrogen peroxide complex.

Peroxides of alkali and alkaline earth metals include lithium peroxide, potassium peroxide, sodium peroxide, magnesium peroxide, calcium peroxide and barium peroxide. Organic peroxide sources include, for example, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, monoperoxyphthalate and the like.

Peroxy acids and their salts include organic peroxy acids such as alkyl peroxy acids and monoperoxyphthalate, as well as inorganic peroxy acid salts including persulfate, dipersulfate, percarbonate, perphosphate, perborate and persilicate salts of alkali and alkaline earth metals such as lithium, potassium, sodium, magnesium, calcium and barium. Another useful peroxy compound is sodium pyrophosphate peroxyhydrate.

Typically, the peroxide source is selected from: hydrogen peroxide, urea peroxide, sodium percarbonate, sodium perborate, polyvinylpyrrolidone-hydrogen peroxide complex, and mixtures thereof. In a preferred embodiment, the peroxide source is polyvinylpyrrolidone-hydrogen peroxide complex.

Typically, the peroxide source is present in the composition to deliver hydrogen peroxide in an amount of from 0.01 weight % to 5 weight %, from 0.05 weight % to 3 weight %, or from 0.1 weight % to 1 weight %, by total weight of the composition. In some embodiments, the peroxide source is present in the composition to deliver hydrogen peroxide in an amount of from 0.1 weight % to 5 weight %, from 0.1 weight % to 4 weight %, or from 0.1 weight % to 3 weight % by total weight of the composition. Preferably, the peroxide source is present in the composition to deliver hydrogen peroxide in an amount of from 0.1 weight % to 3 weight %, from 0.1 weight % to 2 weight %, or from 0.1 weight % to 1 weight % by total weight of the composition. In some embodiments, the peroxide source is present in the composition to deliver hydrogen peroxide in an amount of from 0.5 weight % to 4 weight %, from 0.5 weight % to 3 weight %, from 0.5 weight % to 2 weight %, or from 0.5 weight % to 1 weight %, by total weight of the composition. Preferably, the peroxide source is present in the composition to deliver hydrogen peroxide in an amount of from 1 weight % to 3 weight %, or from 1 weight % to 2 weight % by total weight of the composition. Typically, the peroxide source is present in the composition to deliver hydrogen peroxide in an amount of 0.1, 1 or 2 weight % by total weight of the composition, on an active ingredient basis.

The compositions of the present invention are typically in liquid form. In some embodiments, the compositions may be provided as a dentifrice, a whitening gel, a mouthwash or a mouthrinse, a spray, an oral strip, a chewing gum or a lozenge.

Optional Ingredients

The oral care compositions of the present invention may further comprise additional ingredients. These additional ingredients may include, but are not limited to, diluents, pH modifying agents, other surfactants, desensitizing agents, tartar control agents, binders, thickening agents, detergents, adhesion agents, foam modulators, mouth feel agents, humectants, sweeteners, flavorants, colorants, antioxidants, sources of fluoride ions, and mixtures thereof. Such ingredients and the amounts in which they could be incorporated would be known to those skilled in the art of oral care. However, non-limiting examples of these ingredients are provided below.

The compositions may comprise one or more further surfactants in addition to those of the surfactant system having an HLB value of from 4 to 13. However, preferably, the compositions do not comprise any other surfactant other than those of the surfactant system.

The compositions provided herein optionally incorporate one or more desensitizing agents. These include, without limitation, potassium salts such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, e.g., from about 0.5 weight % to about 20 weight % by total weight of the composition, depending on the agent chosen. The compositions defined herein may also be used to treat hypersensitivity by blocking dentin tubules when applied to a tooth surface.

The compositions provided herein may optionally include tartar control agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$, sodium tripolyphosphate, long chain polyphosphates such as sodium hexametaphosphate and cyclic phosphates such as sodium trimetaphosphate.

The compositions provided herein may further comprise a binder. Any conventional binder may be utilized. Suitable binding agents include marine colloids; carboxyvinyl polymers; carrageenans; starches; cellulosic polymers such as hydroxyethylcellulose. carboxymethylcellulose (carmellose), hydroxypropyl methyl cellulose, and salts thereof (e.g., carmellose sodium); natural gums such as karaya, xanthan, gum arabic and tragacanth; chitosan; colloidal magnesium aluminum silicate; and colloidal silica. Preferably, a binder is present in the composition in an amount from 0.1 weight % to 5 weight % by total weight of the composition.

Thickening agents which may be incorporated into the compositions defined herein include natural and synthetic gums and colloids. Suitable thickening agents include naturally occurring polymers such as carrageenan, xanthan gum, polyglycols of varying molecular weights sold under the tradename Polyox, and polyvinylpyrrolidone. Compatible inorganic thickening agents include amorphous silica compounds and colloidal silica compounds available under the trade designation Cab-o-sil manufactured by Cabot Corporation. Other inorganic thickening agents include natural and synthetic clays such as hectorite clays, lithium magnesium silicate (laponite) and magnesium aluminum silicate (Veegum).

The compositions defined herein may optionally comprise one or more adhesion agents. The adhesion agent may by a polymeric adherent material. The polymeric adherent material may be any agent that attaches to the surface of a mammalian tooth and/or to a heterogeneous biofilm which also may be present on a tooth's surface. Attachment may occur by any means, such as ionic interaction, van der Waals forces, hydrophobic-hydrophilic interactions, etc. The adherent material may be, for example, any homopolymers or copolymers (hereinafter referred to collectively as a "polymers") that adhere to the surface of a tooth. Such polymers may include cellulose polymers, for example one or more hydroxyalkyl cellulose polymers, such as hydroxypropylmethyl cellulose (HPMC), hydroxyethylpropyl cellulose (HEPC), hydroxybutylmethyl cellulose (HBMC), and carboxymethyl cellulose (CMC). Preferably, the polymeric adherent material comprises at least one cellulose material, for example sodium carboxymethyl cellulose.

The polymeric adherent material may alternatively or additionally include poly (ethylene oxide) polymers (such as POLYOX from Dow Chemical), linear PVP and cross-linked PVP, PEG/PPG copolymers (such as BASF Pluracare L1220), ethylene oxide (EO)—propylene oxide (PO) block copolymers (such as polymers sold under the trade mark Pluronic available from BASF Corporation), ester gum, shellac, pressure sensitive silicone adhesives (such as BioPSA from Dow-Corning), methacrylates, or mixtures thereof. In one embodiment, a copolymer comprises (PVM/MA). Optionally, the copolymer may be selected from the group consisting of: poly (methylvinylether/maleic anhydride), or poly (methylvinylether/maleic acid), or poly (methylvinylether/maleic acid) half esters, or poly (methylvinylether/maleic acid) mixed salts.

Polymers of any molecular weight may be used, including, for example molecular weights of 50,000 to 500,000 Da, 500,000 to 2,500,000 Da or 2,500,000 to 10,000,000 Da (calculated by either number average or weight average).

The oral care compositions defined herein also may include a foam modulator. Foam modulators typically increase the amount of foam produced, for example, when the oral cavity is brushed using the composition in accordance with the methods defined herein. Illustrative examples of foam modulators that increase the amount of foam include, but are not limited to polyoxyethylene and certain polymers including alginate polymers.

The foaming agent is preferably in the oral care composition in an amount from 0.05 to 0.5 weight %, or from 0.1 to about 0.2 weight % by total weight of the composition.

Polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of from 200,000 to 7,000,000 Da, and preferably from 600,000 to 2,000,000 Da, and more preferably from 800,000 to 1,000,000 Da. Polyox® is the trade name for the high molecular weight polyoxyethylene produced by Union Carbide.

Preferably, the compositions provided herein further comprise at least one pH modifying agent. Such agents include acidifying agents to lower pH, basifying agents to raise pH, and buffering agents to control pH within a desired range. The pH modifying agent preferably comprises a basifying agent and/or a buffering agent. For example, one or more compounds selected from acidifying, basifying and buffering agents can be included to provide a pH of 2 to 10, or in various illustrative embodiments, a pH of 2 to 8, 3 to 9, 4 to 8, 5 to 7, 6 to 10, or 7 to 9. Any orally acceptable pH modifying agent can be used including, without limitation, carboxylic, phosphoric and sulfonic acids, acid salts (e.g., monosodium citrate, disodium citrate, monosodium malate); alkali metal hydroxides such as sodium hydroxide; carbonates such as sodium carbonate, bicarbonates, and sesquicarbonates; borates; silicates; phosphates (e.g., monosodium phosphate, trisodium phosphate, pyrophosphate salts), imidazole and the like. One or more pH modifying agents are preferably present in a total amount effective to maintain the composition in an orally acceptable pH range.

Mouth-feel agents that may be incorporated into the compositions used in the methods defined herein include materials which impart a desirable texture or other feeling during use of the composition. Such agents include bicarbonate salts, which may impart a "clean feel" to teeth and gums due to effervescence and release of carbon dioxide. Any orally acceptable bicarbonate can be used, including, without limitation, alkali metal bicarbonates such as sodium and potassium bicarbonates, ammonium bicarbonate, and mixtures thereof. One or more bicarbonate salts are optionally present in a total amount of from 0.1 weight % to 20 weight %, for example from 1% to 15 weight %, by total weight of the composition.

The compositions provided herein may optionally comprise a sweetener. Sweeteners which may be used in the compositions of the present invention include artificial sweeteners such as saccharin, acesulfam, neotam, cyclamate or sucralose; natural high-intensity sweeteners such as thaumatin, stevioside or glycyrrhizin; or sugar alcohols such as sorbitol, xylitol, maltitol or mannitol. These may be present in an amount of up to 0.5 weight %, optionally from 0.005 weight % to 0.1 weight %, based on the total weight of the composition.

The compositions provided herein may optionally comprise a flavorant. Flavorants that may be used in the compositions of the present invention include essential oils as well as various flavoring aldehydes, esters, alcohols, and similar materials. Examples of the essential oils include oils of spearmint, peppermint, aniseed, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint. The flavourant may be incorporated in the composition in an amount of from 0.1 weight % to 5 weight %, or from 0.5 weight % to 1.5 weight %, by total weight of the composition.

The compositions provided herein may comprise at least one colorant. Colorants herein include pigments, dyes and agents imparting a particular luster or reflectivity such as pearling agents. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. One or more colorants are optionally present in a total amount of from 0.001 weight % to about 20 weight %, for example, from 0.01 weight % to 10 weight %, or from 0.1 weight % to 5 weight %, by total weight of the composition.

Preservatives, such as chlorhexidine, triclosan, quaternary ammonium compounds (such as benzalkonium chloride) or parabens (such as methyl or propyl paraben) may be incorporated in the compositions used in the methods of the present invention. The amount of preservative is typically up to 0.5 weight %, optionally from 0.05 to 0.1 weight %, by total weight of the composition.

Preferably, the compositions defined herein comprise a fluoride ion source. Fluoride ion sources include, but are not limited to: stannous fluoride, sodium fluoride, potassium fluoride, potassium monofluorophosphate, sodium monofluorophosphate, ammonium monofluorophosphate, sodium fluorosilicate, ammonium fluorosilicate, amine fluoride such as olaflur (N'-octadecyltrimethylendiamine-Nionic,N,N'-tris(2-ethanol)-dihydrofluoride), ammonium fluoride, and combinations thereof. Optionally, the fluoride ion source includes stannous fluoride, sodium fluoride, amine fluorides, sodium monofluorophosphate, as well as mixtures thereof. Preferably, the oral care composition of the invention may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions used in the invention in an amount of from 0.001 weight % to 10 weight %, e.g., from 0.003 weight % to 5 weight %, or from 0.01 weight % to 1 weight % or to 0.05 weight %. However, it is to be understood that the weights of fluoride salts to provide the appropriate level of fluoride ion will vary based on the weight of the counter ion in the salt, and one of skill in the art may readily determine such amounts. A preferred fluoride salt may be sodium fluoride.

Methods of Use

The present inventors have unexpectedly found that in an oral care composition comprising a peroxide source and a carrier comprising a polyhydric alcohol, the peroxide may be stabilized when a surfactant, or combination of surfactants, having an HLB value of from 4 to 13, is incorporated into the composition.

Accordingly, in one arrangement, there is provided a use of a surfactant system having an HLB value of from 4 to 13 to stabilize a peroxide source in an oral care composition, wherein the composition comprises, in addition to the peroxide source and the surfactant system having an HLB value of from 4 to 13, a polyhydric alcohol, wherein the combined amount of the polyhydric alcohol and the surfactant system is from 60 weight % to 95 weight % by total weight of the composition, and wherein the weight ratio of the polyhydric alcohol to the surfactant is from 9:1 to 1:4.

The composition (and particularly, the surfactant system, the polyhydric alcohol, the peroxide source, and their amounts/ratios) may be as defined herein.

In another arrangement, there is provided a method of stabilizing a peroxide source in an oral care composition comprising the peroxide source and a polyhydric alcohol, the method comprising incorporating a surfactant system having an HLB value of from 4 to 13 into the composition, wherein the combined amount of the polyhydric alcohol and the surfactant system is from 60 weight % to 95 weight % by total weight of the composition, and wherein the weight ratio of the polyhydric alcohol to the surfactant is from 9:1 to 1:4.

The composition (and particularly, the surfactant system, the polyhydric alcohol, the peroxide source, and their amounts/ratios) may be as defined herein.

The following Examples illustrate methods of the invention and their uses. The Examples are illustrative and do not limit the scope of the invention.

EXAMPLES

Example 1—Hydrogen Peroxide Stability (1)

14.3% liquid hydrogen peroxide (35% active, technical grade) was mixed with 85.7% liquid carrier comprising propylene glycol (PG) and propylene glycol mono-caprylate (PMC; Capryol 90®) which has an HLB value of 6, in varying weight ratios to obtain a final peroxide concentration of 5%. A composition comprising PG and peroxide alone was used as a control for the experiment. The liquid solutions were stored in glass jars at 60° C. for several weeks. The peroxide concentration was titrated each week to assess stability. Hydrogen peroxide titration was conducted based on a standard method. Briefly, each sample was weighed accurately in a 250 ml flask. 5 ml 25% potassium iodide, 25 ml glacial acetic acid, 50 ml water, and 2 drops of ammonium molybdate were added into the flask. The contents of the flask were mixed using a magnetic stir bar. The sample was subsequently titrated with 0.1N sodium thiosulfate solution until the yellow color has almost disappeared. Then, 2 ml of starch indicator solution were added to the flask. Titration with sodium thiosulfate was continued slowly until the purple/black color disappeared. This marked the end point of the titration. The compositions tested and results are illustrated in Table 1.

TABLE 1

Results of hydrogen peroxide stability test

| Time (weeks) | PG | PG/PMC 9:1 | PG/PMC 7:3 | PG/PMC 1:1 |
| --- | --- | --- | --- | --- |
| 0 | 4.94 | 4.94 | 5.01 | 5.00 |
| 1 | 4.33 | 4.83 | 4.80 | 4.68 |
| 2 | 3.44 | 4.65 | 4.33 | 4.85 |
| 3 | 2.77 | 3.35 | 4.22 | 4.62 |
| 4 | 1.68 | 2.56 | 3.56 | 4.12 |
| 5 | 1.31 | 1.98 | 3.14 | 3.84 |
| 6 | 0.91 | 1.41 | 2.48 | 3.16 |

As can be seen from Table 1, peroxide stability was enhanced in the presence of PMC surfactant, in a concentration-dependent manner. It may be concluded that by introducing hydrophobicity into the liquid carrier, peroxide may be stabilized.

Example 2—Polyvinylpyrrolidone (PVP)-Peroxide Stability 16.7% hydrogen peroxide-PVP complex (18% active, technical grade) was mixed with 83.3% liquid carrier comprising propylene glycol (PG) and propylene glycol mono-caprylate (PMC; Capryol 90®) which has an HLB value of 6 in varying weight ratios to obtain a final peroxide concentration of 3%. The liquid solutions were stored in glass jars at 60° C. for six weeks and the peroxide was titrated as described in Example 1 to assess stability. The compositions tested and results are illustrated in Table 2.

TABLE 2

Results of peroxide-PVP stability test

| Time (weeks) | PG | PG/PMC 9:1 | PG/PMC 7:3 | PG/PMC 1:1 |
| --- | --- | --- | --- | --- |
| 0 | 2.96 | 2.98 | 3.02 | 3.09 |
| 1 | 2.68 | 2.94 | 2.97 | 2.95 |
| 2 | 1.84 | 2.65 | 3.06 | 3.05 |
| 3 | 1.28 | 1.94 | 2.62 | 2.73 |
| 4 | 0.60 | 1.23 | — | 2.75 |
| 5 | 0.40 | 0.73 | — | 2.65 |
| 6 | 0.13 | 0.53 | — | 2.67 |

As can be seen from Table 2, peroxide stability was enhanced in the presence of PMC surfactant, when complexed with PVP, in a concentration-dependent manner. It may be concluded that by introducing hydrophobicity into the liquid carrier, peroxide, in a complexed or uncomplexed form, may be stabilized.

Example 3—Hydrogen Peroxide Stability (2)

16.7% hydrogen peroxide-PVP complex (18% active, technical grade) was mixed with 83.3% liquid carrier comprising propylene glycol (PG) and propylene glycol monocaprylate (PMC; Capryol 90®) which has an HLB value of 6 in a PG:PMC weight ratio of 7:3, or a combination of propylene glycol and sorbitan laurate (Span 20®) which has an HLB value of 8.6 in a PG:Span20 weight ratio of 7:3. or a combination of propylene glycol and PEG-8 glyceride (PEG) which has an HLB value of 14 in a PG:PEG weight ratio of 7:3. The liquid solutions were stored in glass jars at 60° C. for three weeks and the peroxide was titrated as described in Example 1 to assess stability. The results are illustrated in Table 3.

TABLE 3 results of hydrogen peroxide stability (2)

| Time (weeks) @ 60 C. | PG/Capryol 90 (HLB 5) | PG/PEG-8 Glyceride (HLB 14) | Span 20 | PG |
|---|---|---|---|---|
| 0 | 3.05 | 2.87 | 3.00 | 2.99 |
| 1 | 2.9 | 2.45 | 2.75 | 2.65 |
| 2 | 2.83 | 1.54 | 2.38 | 1.75 |
| 3 | 2.62 | 0.88 | 2.32 | 1.28 |

As can be seen from Table 3, peroxide stability was enhanced in the presence of PMC surfactant which has an HLB value of 6 and in the presence of Span 20 which has an HLB value of 8.6. However, peroxide-stabilizing effects were not observed with PEG-8 Glyceride which has an HLB value of 14.

Whilst particular embodiments of the invention have been illustrated and described, it will be obvious to those skilled in the art that various changes and modifications may be made without departing from the scope of the invention as defined in the appended claims.

What is claimed is:

1. An oral care composition comprising a peroxide source, a polyhydric alcohol and a surfactant system having an HLB value of from 4 to 13,
   wherein the combined amount of the polyhydric alcohol and the surfactant system is from 60 weight % to 95 weight % by total weight of the composition,
   and wherein the weight ratio of the polyhydric alcohol to the surfactant system is from 9:1 to 1:4.

2. The composition of claim 1, wherein the polyhydric alcohol is selected from propylene glycol, polyethylene glycol, glycerin, and mixtures thereof.

3. The composition of claim 2, wherein the polyhydric alcohol is propylene glycol.

4. The composition of claim 1, wherein the surfactant has an HLB value of from 4 to 9.

5. The composition of claim 4, wherein the surfactant system has an HLB value of from 5 to 8.

6. The composition of claim 1, wherein the weight ratio of the polyhydric alcohol to the surfactant system is from 9:1 to 1:2.

7. The composition of claim 6, wherein the weight ratio of the polyhydric alcohol to the surfactant system is from 9:1 to 1:1.

8. The composition of claim 7, wherein the weight ratio of the polyhydric alcohol to the surfactant system is from 7:3 to 1:1.

9. The composition of claim 8, wherein the weight ratio of the polyhydric alcohol to the surfactant system is from 3:2 to 1:1.

10. The composition of claim 1, wherein the combined amount of the polyhydric alcohol and the surfactant system is from 70 weight % to 95 weight % by total weight of the composition.

11. The composition of claim 1, wherein the combined amount of the polyhydric alcohol and the surfactant system is from 80 to 90 weight %, by total weight of the composition.

12. The composition of claim 11, wherein the combined amount of the polyhydric alcohol and the surfactant system is from 85 weight % to 90 weight % by total weight of the composition.

13. The composition of claim 1, wherein the surfactant system having an HLB value from 4 to 13 comprises a non-ionic surfactant.

14. The composition of claim 13, wherein the surfactant system having an HLB value of from 4 to 13 comprises propylene glycol monocaprylate.

15. The composition of claim 1, wherein the surfactant system having an HLB value of from 4 to 13 comprises sorbitan laurate.

16. The composition of claim 15, wherein the surfactant system having an HLB value from 4 to 13 comprises polyethylene glycol caprylate/caprate glyceride.

17. The composition of claim 1, wherein the peroxide source is selected from: hydrogen peroxide, urea peroxide, sodium percarbonate, sodium perborate, polyvinylpyrrolidone-hydrogen peroxide complex, and mixtures thereof.

18. The composition of claim 17, wherein the peroxide source is polyvinylpyrrolidone-hydrogen peroxide complex.

19. The composition of claim 1, wherein the peroxide source is present in the composition to deliver hydrogen peroxide in an amount of 0.1 weight 0/% to 5 weight % by total weight of the composition.

20. The composition of claim 19, wherein the peroxide source is present in the composition to deliver hydrogen peroxide in an amount of 1 weight % to 3 weight % by total weight of the composition.

21. The composition of claim 1, wherein the composition further comprises an agent selected from: surfactants, desensitizing agents, tartar control agents, binders, thickening agents, detergents, adhesion agents, foam modulators, pH modifying agents, mouth feel agents, sweeteners, flavorants, colorants, humectants, fluoride sources and combinations thereof.

22. The composition of claim 1, wherein the composition is selected from whitening gels, mouthwashes, sprays, dentifrices, oral strips, chewing gums and lozenges.

* * * * *